(12) United States Patent
Goodman et al.

(10) Patent No.: US 6,344,179 B1
(45) Date of Patent: Feb. 5, 2002

(54) FLUORALKENYL NORTROPANES

(75) Inventors: Mark M. Goodman, Atlanta, GA (US); Ping Chen, Indianapolis, IN (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/553,795

(22) Filed: Apr. 21, 2000

Related U.S. Application Data (60) Provisional application No. 60/130,836, filed on Apr. 22, 1999.

(51) Int. Cl.[7] .................. A61K 51/00; C07D 451/02
(52) U.S. Cl. ................... 424/1.89; 424/1.85; 546/124; 546/132
(58) Field of Search ............................. 424/1.89, 1.85, 424/1.81; 546/124, 127, 132

(56) References Cited

U.S. PATENT DOCUMENTS

| 5,698,179 A | 12/1997 | Neumeyer et al. ......... 424/1.85 |
| 5,853,696 A | 12/1998 | Elmaleh et al. ............ 424/1.85 |

OTHER PUBLICATIONS

Fishman, A.J. et al. "SPECT Imaging of Dopamine Transporter Sites in Normal and MPTP—Treated Rhesus Monkeys" (1997) *J. Nuc. Med.* 38:144–150.

Giros, B. et al. "Hyperlocomotion and indifference to cocaine and amphetamine in mice lacking the dopamine transporter"; (1996) *Nature* 38:144–150.

Goodman, M.M. *Clinical Positron Emission Tomography* Mosby Yearbook, 1992, K.F. Hubner et al., Chapter 14 "automated Synthesis of Radiotracers for PET Applications".

Goodman, M.M. et al. "Synthesis and Characterization of Radioiodinated N–(3–Iodopropen–1–yl)–2β–carbomethoxy– 3β–(4–chlorophenyl)tropanes: Potential Dopamine Reuptake Site Imaging Agents" (1994) *J. Med. Chem* 37:1535–1542.

Hubner, K.F. *Clinical Positron Emission Tomography* Mosby Year Book, 1992, K.F. Hubner, et al., Chapter 2 "University of Tennessee Biomedical Imaging Center and Transfer of Technology to the Clinical Floor".

Kung, M–P. et al. "IPT: a Novel Iodinated Ligand for the CNS Dopamine Transporter" (1995) *Synapse* 20:316–324.

Malison, R.T. et al. "Striatal Dopamine Transporter Imaging in Nonhuman primates with Iodine–123–IPT SPECT " (1995) *J. Nucl. Med.* 36:2290–2297.

Niznik, H.B. et al. "The Dopamine Transporter is Absent in Parkinsonian Putamen and Reduced in the Caudate Nucleus" (1991) *J. Neurochem.* 56:192–198.

*Primary Examiner*—Michael G. Hartley
(74) *Attorney, Agent, or Firm*—Greenlee, Winner and Sullivan, P.C.

(57) ABSTRACT

Provided are compounds of the following formula:

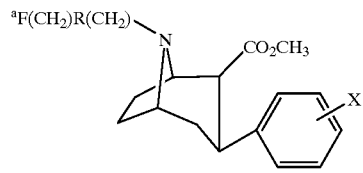

wherein R is C2–C6 mono- or multi-unsaturated hydrocarbon having one or more ethylene, acetylene or allene groups, A is 18 or 19, and X is H or halogen.

The compounds of the invention bind to dopamine transporter with high affinity and selectivity and are thus useful as diagnostic and therapeutic agents for diseases associated with dopamine transporter dysfunction. The radiolabeled compounds are useful as imaging agents for visualizing the location and density of dopamine transporter by PET imaging.

26 Claims, 2 Drawing Sheets

FLUORALKENYL NORTROPANES

CROSS-REFERENCE TO RELATED APPLICATIONS

This application claims priority to provisional application No. 60/130,836 filed Apr. 22, 1999.

ACKNOWLEDGMENT OF FEDERAL RESEARCH SUPPORT

This invention was made, at least in part, with funding from the United States Department of Energy under contract #DE-FG02-97ER-62367. Accordingly, the U.S. government may have certain rights in this invention.

BACKGROUND OF THE INVENTION

The invention includes novel chemical compounds having specific binding in a biological system and capable of being used for positron emission tomography (PET).

The ability of analog compounds to bind to localized ligands within the body makes it possible to utilize such compounds for in situ imaging of the ligands by PET, SPECT and similar imaging methods. In principle, nothing need be known about the nature of the ligand, as long as binding occurs, and such binding is specific for a class of cells, organs, tissues or receptors of interest. PET imaging is accomplished with the aid of tracer compounds labeled with a positron-emitting isotope (Goodman, M. M. *Clinical Positron Emission Tomography*, Mosby Yearbook, 1992, K. F. Hubner et al., Chapter 14). For most biological materials, suitable isotopes are few. The carbon isotope, $[^{11}C]$, has been used for PET, but its short half-life of 20.5 minutes limits its usefulness to compounds that can be synthesized and purified quickly, and to facilities that are proximate to a cyclotron where the precursor $[^{11}C]$ starting material is generated. Other isotopes have even shorter half-lives. $[^{13}N]$ has a half-life of 10 minutes and $[^{15}O]$ has an even shorter half-life of 2 minutes. The emissions of both are more energetic than those of $[^{11}C]$. Nevertheless, PET studies have been carried out with these isotopes (Hubner, K. F., in *Clinical Positron Emission Tomography*, Mosby Year Book, 1992, K. F. Hubner, et al., Chapter 2). A more useful isotope, $[^{18}F]$, has a half-life of 110 minutes. This allows sufficient time for incorporation into a radio-labeled tracer, for purification and for administration into a human or animal subject. In addition, facilities more remote from a cyclotron, up to about a 200 mile radius, can make use of $[^{18}F]$ labeled compounds. Disadvantages of $[^{18}F]$ are the relative scarcity of fluorinated analogs that have functional equivalence to naturally-occurring biological materials, and the difficulty of designing methods of synthesis that efficiently utilize the starting material generated in the cyclotron. Such starting material can be either fluoride ion or fluorine gas. In the latter case only one fluorine atom of the bimolecular gas is actually a radionuclide, so the gas is designated $^{18}F$-F. Reactions using $^{18}F$-F as starting material therefore yield products having only one half the radionuclide abundance of reactions utilizing $K^{18}F$ as starting material. On the other hand, $[^{18}F]$ can be prepared in curie quantities as fluoride ion for incorporation into a radiopharmaceutical compound in high specific activity, theoretically 1.7 Ci/nmol using carrier-free nucleophilic substitution reactions. The energy emission of $[^{18}F]$ is 0.635 MeV, resulting in a relatively short, 2.4 mm average positron range in tissue, permitting high resolution PET images.

Use of $[^{18}F]$ labeled compounds in PET has been limited to a few analog compounds. Most notably, $[^{18}F]$-fluorodeoxyglucose has been widely used in studies of glucose metabolism and localization of glucose uptake associated with brain activity. $[^{18}F]$-L-fluorodopa and other dopamine receptor analogs have also been used in mapping dopamine receptor distribution.

Other halogen isotopes can serve for PET or for conventional tracer labeling. These include $^{75}Br$, $^{76}Br$, $^{77}Br$ and $^{82}Br$ which have usable half-lives and emission characteristics. In general, the chemical means exist to substitute any halogen moiety for the described isotopes. Therefore, the biochemical or physiological activities of any halogenated homolog of the described compounds are now available for use by those skilled in the art, including stable isotope halogen homologs. Astatine can be substituted for other halogen isotopes; $[^{210}At]$ emits alpha particles with a half-life of 8.3 h. At-substituted compounds are therefore useful for tumor therapy, where binding is sufficiently tumor-specific.

Dopamine transporters (DAT) are proteins that reside on the membrane of the nerve terminals of the presynaptic mesolimbic dopaminergic neurons. The DAT serves to remove dopamine from the synapse, a process which helps regulate central nervous system (CNS) dopamine neurotransmission. A decrease in DAT density in the striatum has been associated with Parkinson's disease. Inhibition of the re-uptake of dopamine at the DAT has been implicated with the reinforcing properties of cocaine.

Abnormalities in CNS dopaminergic neurotransmission have been implicated in movement disorders such as Parkinson's disease. This disorder has been shown to be caused by a significant decrease in the synthesis and transmission of dopamine which results from a degeneration of dopamine neurons in the substantia nigra and striatum. Drugs such as levodopa have been found to provide a clinical benefit only early in the course of Parkinson's disease by supplementing the brain's supply of dopamine. During the progression of the disease the effectiveness of drug therapy diminishes. Efforts to identify potentially more Gleffective therapeutic strategies for preventing or slowing degeneration of dopamine neurons has resulted in the development of neuroprotective agents. Monoamine oxidase inhibitors such as deprenyl appeared in early clinical trials to provide some benefit. A potentially more promising therapy for patients with Parkinson's disease is transplantation of human fetal mesencephalic tissue. The implantation of human fetal brain tissue in a small number of patients has been reported to result in the improvement of their overall functions. Longitudinal studies with a radiopharmaceutical for providing quantitative information on dopamine neuronal density using imaging technology would be valuable in determining the efficacy of the therapeutic strategies described above. In vivo imaging studies in normal volunteersand patients with Parkinson's disease using positron emission tomograph (PET) involving 6-$[^{18}F]$fluorodopa has provided a measure of dopamine synthesis and storage in vesicles of presynaptic neurons in the basal ganglia. However, a significant amount of peripheral $[^{18}F]$fluorodopa metabolism, transport and nonspecific binding of radiometabolites in the brain result in low striatal to cerebellum ratios of 2:1. Loss of dopaminergic neurons in the substantia nigra in patients with Parkinson's disease has also shown to result in a corresponding loss of dopamine transporter sites in the membrane of striatal presynaptic dopaminergic neurons. Because the dopamine transporter plays a pivotal role in dopamine neurotransmission, the development of radiopharmaceuticals radiolabeled with positron emitting isotopes which exhibit pronounced brain uptake, very high selectivity and affinity for the transporter, and low nonspecific binding would be excellent for the measurement of the density of presynaptic dopamine transporter sites by positron emission tomography. To meet this need, the present application discloses a new series of brain imaging agents, typical of which are (N-CE)4'-fluorobut-2-en-1-yl-2β-carbomethoxy-3β-(4-substituted-phenyl)nortropane (FBNT) and (n-(E)-4'-fluorobut-2-en-1-yl-2β-carbomethoxy-3β-(4-chlorophenyl) nortropane (FBCINT). When labeled with the positron emitting radioisotope fluorine-18, a compound of the invention can be used as a diagnostic imaging agent to measure CNS neuronal function in the brain of a patient suffering from Parkinson's disease and cocaine addiction.

SUMMARY OF THE INVENTION

The invention provides fluoroalkenyl nortropanes having the following general structure (Formula I):

where R is $C_2$–$C_6$ mono- or multi-unsaturated hydrocarbon having one or more ethylene, acetylene or allene groups,
a is 18 or 19, and
X is H or halogen Compounds of the invention bind specifically and preferentially to dopamine transporter (DAT). $^{18}$F-labeled compounds of the invention are useful for positron emission tomography (PET) imaging of dopaminergic neurons. Unlabeled compounds have pharmacological utility as cocaine analogs. Both E and Z isomers of the alkenyl moiety can be synthesized. Substituents on the phenyl ring can be H or halogen. The invention is described in detail by reference to an exemplary compound having an F-butenyl group substituted on the bridge nitrogen. CR is $C_2H_2$.

Examples of suitable R groups include:

compound can be purified to high specific activity. As a result, the useable half-life of the isotope has been maximized.

Methods are provided for conducting positron emission tomography imaging of a subject comprising:
1) administering to the subject an image-generating amount of a compound of formula I which contains at least one radioactive halogen and
2) measuring the distribution within the subject of the compound by positron emission tomography.

DETAILED DESCRIPTION OF THE INVENTION

In general the terms and phrases used herein have their art-recognized meaning, which can be found by reference to standard texts, journal references and contexts known to those skilled in the art. The following definitions are provided to clarify their specific use in the context of the invention.

and the like, including both E and Z isomers, where possible.

In particular are provided compounds wherein R is CH═CH, a is 18, and X is selected from the group consisting of H, Br, Cl, I and F in the 4' position.

Methods of synthesis are described that permit last step substitution of the halogen radiolabel such that the final The term "halogen" refers to radioactive and nonradioactive isotopes of fluorine, chlorine, bromine, iodine, and astatine. These include F, $^{18}$F, $^{19}$F, Cl, $^{35}$Cl, Br, $^{75}$Br, $^{76}$Br, $^{77}$Br, $^{82}$Br, I, $^{123}$I, $^{124}$I, $^{125}$I, $^{131}$I, At, $^{210}$At and $^{211}$At.

Alkenes are unsaturated hydrocarbons which contain a carbon-carbon double bond. "Ethylene" as used herein refers to the simplest alkene with a formula of $C_2H_4$. Alkynes are unsaturated hydrocarbons containing a triple carbon-carbon bond. The simplest alkyne is $C_2H_2$, commonly called "acetylene". "Allene" as used herein refers to unsaturated hydrocarbon which contain two adjacent carbon-carbon double bonds. The examples of alkenes, alkynes, and allenes useful for the invention include, but are not limited to, the following:

that N-(E)-4'-fluorobut-2-en-1-yl-2β-carboalkoxy-3β-4 (chlorophenyl)nortropane (FBCINT) or an analog is an excellent radiopharmaceutical for the diagnosis and management of treatment of Parkinson's disease and the management of treatment of cocaine addiction in humans using emission topographic techniques.

A new series of fluoroalkenyl nortropanes of formula I were developed with the following substitutions; R is $C_2$–$C_6$ mono- or multi-unsaturated hydrocarbon having one or more ethylene, acetylene or allene groups, a is 18 or 19, and X is H or halogen.

Preferred compounds for use in diagnosis and/or imaging, e.g. PET, are compounds of formula 1 containing an $^{18}F$-butenyl group substituted on the bridge nitrogen.

Unlabeled compounds of formula I have pharmacological utility as cocaine analogs.

Particularly preferred compounds of the invention include (n-(E)4'-fluorobut-2-en-1-yl-2β-carbomethoxy-3β-(4-substituted-phenyl)nortropane (FBNT) and (n-(E)yl-2β-carbomethoxy-3 β(4-chlorophenyl)nortropane (FBCINT). When labeled with the positron emitting radioisotope fluorine-18, these compounds can be used as a diagnostic imaging agent to measure CNS neuronal function in the brain of patients suffering from parkinson's disease and cocaine addition. These tropanes were designed to bind to the dopamine transporter (DAT) with high affinity. A unique characteristic of this class of radiopharmaceuticals is incorporation of fluorine-18 on N-(E)4' fluorobut-2-en-1-yl group.

FBCINT was found to be stable to metabolism and in vivo loss of the fluorine-18 radioisotope. Competitive binding assays demonstrated that FBCINT had a Ki (nM) of 2.4 nM in cells stably transfected with human DAT using [H-3]WIN 35,428 a potent dopamine transporter ligand. Binding to the serotonin transporter (SERT) in cells stably transfected with human SERT using [H-3]citalopram afforded Ki (nM) of 12.1. Following tail vein injection in rats, [F-18]FBCINT showed good striatum (S) uptake (2.5% dose/g at 120 min) with rapid clearance from the cerebellum (CB) and cortex (CX) giving S/CB=15 and SICX=7 at 120 min p.i. Preblocking rats with GBR12909 (DAT), paroxetine (SERT) and reboxetine (NET) gave S/CB–3.8, 12 and 11 respectively at 60 min p.i. Brain PET imaging using fluorine-18 labeled FBCINT in a rhesus monkey was performed and showed high S uptake at 180–210 min (2.7 μCi/mL) with rapid CB and CX washout resulting in S/CB=12.9 and S/CX+11.4 at 180–210 min by PET imaging. FBCINT exhibited reversibility. Displacement of FBCINT by βCIT (0–9 μmole/kg) gave a washout half time of 21 min. These data demonstrate Fluorine-18 is the most attractive positron emission tomography PET radionuclide (97%) abundant) for radiolabeling because its 110 minute half-life allows sufficient time (3×110 minutes) for incorporation into the radiopharmaceutical and for purification of the final product suitable for human administration. Secondly, fluorine-18 can be prepared in curie quantities as fluoride ion for incorporation into the radiopharmaceutical in high, theoretical 1.7 Ci/nmol, specific activity by no-carrier added nucleophilic substitution reactions. Fluorine-18 is also the lowest energy positron emitter (0.635 MeV, 2.4 mm positron range) which affords the highest resolution images. Finally the 110 minute half-life allows sufficient time for regional distribution up to a 200 mile radius from the manufacturing site.

The brain dopamine transporter (DAT) is critical to dopamine neurotransmission and the psycho-stimulant effects of cocaine [Giros B. et al. (1996) *Nature* 379:606] and decreased by Parkinson's disease [Niznik, H. B. et al. (1991) *J. Neurochem.* 56:192]. A major recent effort has focused on the development of radiolabeled DAT ligands to study the physiology, pharmacology and pathophysiology of the brain DAT using single photon emission tomography (SPECT). Recently, we reported the synthesis, characterization and imaging properties of an iodine-123 DAT imaging agent, (N-((E)-3-[$^{123,125}$I]iodopropen-1-yl)-2β-carbomethoxy-3β-(4-chloro-phenyl)nortropane (MMG-142/IPT) [Goodman, M. M. et al. (1994) *J. Med. Chem.* 37:1535; Kung, M-P. et al. (1995) *Synapse* 20:316; Malison, R. T. et al. (1995) *J. Nucl. Med.* 36:2290]. In comparison to β-CIT, [$^{123}$I]MMG-142/IPT had a higher in vitro selectivity for (DA/5-HT≅7) and superior imaging and pharmacokinetic properties. [$^{123}$I]MMG-142/IPT, demonstrated high (15 to 1) striatal to cerebellum ratios in non-human primates within 2 h post injection (p.i.) and transientequilibriumat30 min p.i. Subsequent to our initial reports several variants, i.e. IACFT [Fishman, A. J. et al. (1997) *J. Nucl. Med.* 38:144], of [$^{123}$I]MMG-142/IPT have been reported which have similar binding affinity and imaging properties. These results suggest that the N-((E)-3-iodopropen-2-yl) moiety at the 8-aza-position is an important pharmacophore that imparts attractive kinetic behavior to these ligands for imaging the dopanmine transporter complex.

MMG-142/IPT

FBNT (6a–e)

A DAT analog of MMG-142/IPT having very similar imaging properties and labeled with fluorine-18 would be of significant value. This objective prompted us to synthesize a series of (N-((E)-4-fluorobut-2-en-1-yl)-2β-carbomethoxy-3β-(4-substituted-phenyl)nortropanes ((FBNT) with replacement of the (N-((E)-3-[$^{123}$I]-iodopropen-1-yl) group with a (N-((E)-4-[$^{18}$F]-fluorobut-2-en-1-yl) bioisostere. We explored the effect of the fluorine substituent on striatal affinity, uptake and retention by the preparation and biological evaluation of several representative 3β-(4-substituted-phenyl)-(N-((E)-4-fluorobut-2-en- 1-yl)nortropane-2β-carboxylic acid esters (6a–e) as potential DAT PET imaging agents.

The synthetic approach for the preparation of (N-((E)-4-fluorobut-2-en-1-yl)-2βcarbomethoxy-3β-(4-substituted-phenyl)nortropanes (FBNT) is delineated in Scheme 1. This scheme provides exemplary synthetic routes for the compounds of this invention, but are in no way limiting. Modifications of the materials and methods can be made by routine choice and without undue experimentation by those of ordinary skill in the art. The preparation of FBNT analogues (6a, c, and e) involved a four-step sequence of reactions. In this synthetic approach methyl anhydroecgonine was treated with a 4-substituted-phenylmagnesium bromide to give the corresponding 2β-carboxymethoxy-3β-(4-substituted-phenyl)tropanes (3a, d and e). The tropanes 3a, d and e were treated with TrocCl followed by Zn to form the corresponding nortropanes 5a, d and e. The nortropanes 5b and c were prepared by treating methyl anhydroecgonine with 4-trimethylsilylphenylmagnesium bromide followed by NCS/KBr and I$_2$/AgBF$_4$ respectively to give tropanes 3b and c. The tropanes 3b and c were treated with TrocCl followed by Zn to form the nortropanes 5b and c. Nortropanes 5a–e were then treated with (E)-1-fluoro-4-tosyloxybut-2-ene to give the corresponding (N-((E)-4-fluorobut-2-en-1-yl)-2β-carbomethoxy-3β-(4-substituted-phenyl) nortropanes (FBNT) (6a–e).Nortropane 5d was treated with (Z)-1-fluoro-4-tosyloxybut-2-ene to give (N-((Z)-4-fluorobut-2-en-1-yl)-2β-carbomethoxy-3β-(4-chlorophenyl) nortropane (Z-FBCINT) (6f).

Scheme 1
Synthesis of FBNT analogs 6a-e
FBNT

6f
FBCINT

In vitro binding studies for FBNT analogues are shown in Table 1. The date from both dog and human kidney cells transfected with human transporters demonstrated that 6a, 6d and 6e had a moderate to high (1.70–7.52 nM) binding affinity for DAT and 14, 10 and 50 times higher selectivity for DAT over SERT respectively. The results from the binding studies demonstrated that 6a, 6d and 6e were the lead candidates for additional studies. Fluorine-18 labeling methods were developed for 6a, 6d and 6e and in vivo tissue distribution studies were performed in rats to determine which ligands possessed the highest striatum to cerebellum ratios and the most desirable in vivo kinetic behavior for measuring DAT occupancy in non-human primates and humans.

TABLE 1

Relative transporter affinity of FBNT DAT ligands in transfected cell lines.

| Y | DAT[1], Ki (nM) | NET[2], Ki (nM) | 5-HTT[3], Ki (nM) |
|---|---|---|---|
| H, 6a | 7.52 | >10,000 | 102 |
| Br, 6b | 0.24 | 91 | 0.85 |
| I, 6c | 0.17 | 57 | 0.21 |
| (E)-Cl, 6d | 2.54 | >10,000 | 24.2 |
| F, 6e | 1.70 | >10,000 | 85.5 |
| (Z)-Cl, 6f | 47.6 | >10,000 | >10,000 |
| MMG/142, IPT | 1.16 | 48.7 | 4.90 |
| Altropane | 0.78 | >10,000 | 55.4 |
| GBR 12909 | 0.6 | — | — |
| Desipramine | — | 0.49 | — |
| Fluvoxamine | — | — | 0.71 |

[1][$^3$H]WIN 35428 as reference for dopamine transporter site.
[2][$^3$H]Nisoxetine for norepinephrine transporter site.
[3][$^3$H]Citalopram for serotonin transporter site.

The radiosynthetic method used to prepare [$^{18}$F](6a, d and e) is outlined in Scheme 2. We chose a two step method to prepare [$^{18}$F]6d. Commercially available 2-butyne-1,4-diol was reacted with LiAlH$_4$ to give (E)-2-butene-1,4-diol. The diol was treated with p-toluenesulfonyl chloride/t-BuONa to give the labeling substrate (E)-1,4-ditosyloxybut-2-ene. The ditosylate was treated with 626 mCi NCA K[$^{18}$F]/K222 for 10 minutes in 1 mL of CH$_3$CN at 85° C. to give 2-ene after passage onto a Waters silica Seppak followed by elution with 8 mL ether. 1-[$^{18}$F]fluoro-4-tosyloxybut-2-ene was reacted with requisite 2β-carbomethoxy-3β-(4-halophenyl) nortropanes (5a, d and e) in DMF at 135° C. for 45 minutes. HPLC purification on a Waters C$_{18}$RP 25 mm×100 mm, 77.5:22.5:0.1 CH$_3$OH:H$_2$O:NEt$_3$, flow rate 6 mL/min afforded [$^{18}$F](6a, d and e) in 10% RCY E.O.B. in a total synthesis time of 133 minutes with a specific activity of 2.0 Ci/μmol (E.O.B.).

Scheme 2
Synthesis of [$^{18}$F](6a, d and e)

(E)—TsOCH$_2$CH=CHCH$_2$OTs ⟶ (E)—TsOCH$_2$CH=CHCH$_2^{18}$F

↓ 5a,d,e a: X=H
d: X=Cl
e: X=F

[$^{18}$F]6a,d,e

Further provided by this invention is a kit for the rapid syntheses of the compounds of Formula I. The kit includes a compound of Formula II capable of reacting with a reagent capable of displacing L and replacing L with a substituent containing a radioactive group.

Formula 11

L is a leaving group, as understood by those of ordinary skill in the art, and can be displaced by a substituent containing radioactive halogen. The compounds made by this kit can be used for diagnostics and imaging and hence preferably contain a radioactive isotope of a halogen, preferably $^{18}$F.

The longer-lived isotopes, such as $^{123}$I with a half-life of 13 hours, are commercially available from sources such as Nordion International Ltd. (Vancouver, B.C., Canada) or NEN/DuPont (N. Billerica, Mass.). Shorter-lived isotopes, such as $^{18}F$ can be obtained from a regional source, with a ~200 mile radius of the site of intended use.

The described kit is intended for use with a reagent capable of displacing L and replacing L with a substituent containing a radioactive group. An example is described in Scheme II in which a hydrogen (leaving group, L) is replaced by a substituent, —$CH_2CH$=$CHCH_2$ $^{18}F$.

Optionally, the kit can include items of apparatus, such as a reaction vessel, device for transferring isotopic material to the reaction vessel, pre-packed separation column for separating product from excess reactants, shielding and the like, as known in the art. See, e.g., Zea-Ponce, U., et al. (1998) *J. Nuclear Med.* 36:525–529.

The in vivo regional brain tissue distribution of [$^{18}F$] (6a) (Table 2) [$^{18}F$](6d) (Table 3) and [$^{18}F$](6e) (Table 5) were compared in rats. E-[$^{18}F$]FBCINT (6d), the biosostere of MMG-142/IPT, showed the highest retention in the striatum with 50% clearance at 120 minutes when compared to 5 minutes post injection. [$^{18}F$]6d also exhibited the highest striatum to cerebellum ratios 6.89 at 30 minutes post injection. [$^{18}F$]6a, the analog with the lowest Ki for DAT, showed the most rapid washout from striatal tissue with 75% and 90% clearance at 60 and 120 minutes, respectively when compared to 5 minutes post injection. [$^{18}F$]6a also exhibited the lowest striatum to cerebellum ratios 3.0 at 30 minutes post injection. Analog [$^{18}F$]6e, the biosostere of altropane, also showed rapid washout from striatal tissue with 70% and 85% clearance at 60 and 120 minutes, respectively when compared to 5 minutes post injection. [$^{18}F$]6e exhibited higher striatum to cerebellum ratios, 3.5 at 30 minutes post injection, than [$^{18}F$]6a.

TABLE 2

Regional uptake (% dose/g) of radioactivity in brains of unfasted male Sprague Dawley rats (n = 3–4) following intravenous administration of E-[$^{18}F$] FBNT (6a)

| Region | 5 min | 30 min | 60 min | *60 min RTI-113 | 120 min |
|---|---|---|---|---|---|
| Striatum | 1.25 | 0.36 | 0.25 | 0.11 | 0.13 |
| | (0.88–1.47) | (0.30–0.40) | (0.22–0.28) | (0.1–0.11) | (0.09–0.18) |
| Cortex (Cx) | 0.84 | 0.19 | 0.13 | 0.10 | 0.09 |
| | (0.67–1.04) | (0.15–0.23) | (0.12–0.14) | (0.09–0.10) | (0.07–0.12) |
| Cerebellum | 0.55 | 0.12 | 0.09 | 0.09 | 0.07 |
| | (0.48–0.65) | (0.23–0.34) | (0.07–1.0) | (0.08–1.0) | (0.06–0.07) |
| Blood | 0.22 | 0.15 | 0.11 | 0.12 | 0.07 |
| | (0.19–0.25) | (0.13–0.18) | (0.10–0.12) | (0.18–0.23) | (0.06–0.08) |
| Brain | 0.58 | 0.13 | 0.09 | 0.07 | 0.07 |
| | (0.48–0.66) | (0.11–0.15) | (0.08–1.0) | (0.06–0.08) | (0.05–0.080 |
| S/Cereb | 2.27 | 3.0 | 2.78 | 1.22 | 1.86 |
| S/Cx | 1.49 | 1.89 | 1.92 | 1.10 | 1.86 |

*5 mg/kg of RTI-113 was i.v. administered 15 minutes prior to E-[$^{18}F$] FBNT (6a).

TABLE 3

Regional uptake (% dose/g) of radioactivity in brains of unfasted male Sprague Dawley rats (n = 3–4) following intravenous administration of E-[$^{18}F$] FBCINT (6d)

| Region | 5 min | 30 min | 60 min | *60 min RTI-113 | 120 min |
|---|---|---|---|---|---|
| Striatum | 1.33 | 1.31 | 0.61 | 0.15 | 0.69 |
| | (1.0–1.6) | (1.11–1.54) | (0.49–0.83) | (0.14–0.16) | (0.64–0.73) |
| Cortex (Cx) | 0.76 | 0.40 | 0.13 | 0.14 | 0.24 |
| | (0.72–0.87) | (0.26–0.54) | (0.09–0.16) | (0.13–0.15) | (0.18–0.36) |
| Cerebellum | 0.52 | 0.19 | 0.10 | 0.12 | 0.13 |
| | (0.48–0.59) | (0.17–0.22) | (0.05–1.4) | (0.11–0.15) | (0.11–0.14) |
| Blood | 0.14 | 0.16 | 0.10 | 0.12 | 0.13 |
| | (0.14–0.16) | (0.15–0.17) | (0.05–0.14) | (0.11–0.13) | (0.10–0.15) |
| Brain | 0.66 | 0.29 | 0.14 | 0.12 | 0.17 |
| | (0.60–0.77) | (0.28–0.30) | (0.09–0.21) | (0.15–0.18) | (0.15–0.18) |
| Bone | 0.30 | 0.80 | 1.35 | N/A | 1.9 |
| | (0.25–0.36) | (0.57–0.96) | (1.3–1.4) | | (1.18–2.28) |
| S/Cereb | 2.56 | 6.89 | 6.1 | 1.25 | 5.31 |
| S/Cx | 1.75 | 3.28 | 4.69 | 1.07 | 2.88 |

*5 mg/kg of RTI-113 was i.v. administered 15 minutes prior to E-[$^{18}F$] FBCINT (6d).

TABLE 4

Regional uptake (% dose/g) of E-[$^{18}$F] FBCINT (6d)
in brains of unfasted male Sprague Dawley rats (n = 3–4)
60 minutes following
intravenous administration of 5 mg/kg, i.v., of transporter ligands

| Region | No Block | GBR 12909 | Paroxetine | Reboxetine |
|---|---|---|---|---|
| Striatum* | 6.96 | 1.51 | 4.47 | 6.64 |
|  | (5.98–8.48) | (1.33–1.74) | (3.94–5.16) | (5.96–7.29) |
| Cortex (CX)* | 0.53 | 0.69 | 0.46 | 0.41 |
|  | (0.40–0.66) | (0.61–0.75) | (0.42–0.53) | (0.38–0.47) |
| Prefrontal Cx* | 0.74 | 1.02 | 0.67 | 0.77 |
|  | (0.63–0.89) | (0.97–1.06) | (0.58–0.75) | (0.72–0.82) |
| Olfactory Tubercle* | 5.26 | 1.07 | 5.06 | 5.74 |
|  | (3.65–7.12) | (0.92–1.22) | (4.42–5.52) | (4.93–5.38) |
| Cerebellum | 0.13 | 0.15 | 0.10 | 0.12 |
|  | (0.12–0.14) | (0.13–0.16) | (0.09–0.10) | (0.12–0.13) |

*Dry tissue.

TABLE 5

Regional uptake (% dose/g) of radioactivity in brains of
unfasted male Sprague Dawley rats (n = 3–4)
following intravenous administration of E-[$^{18}$F] FBFNT (6e)

| Region | 5 min | 30 min | 60 min | 60 min RTI-113 | 120 min |
|---|---|---|---|---|---|
| Striatum | 1.15 | 0.56 | 0.36 | 0.15 | 0.18 |
|  | (1.0–1.3) | (0.39–0.75) | (0.27–0.52) | (0.12–0.17) | (0.18–0.19) |
| Cortex (Cx) | 0.90 | 0.29 | 0.23 | 0.16 | 0.14 |
|  | (0.62–1.19) | (0.57–1.00) | (0.35–0.45) | (0.14–0.19) | (0.27–0.41) |
| Cerebellum | 0.58 | 0.16 | 0.12 | 0.12 | 0.10 |
|  | (0.48–0.76) | (0.12–0.22) | (0.12–0.12) | (0.18–0.18) | (0.07–0.11) |
| Blood | 0.19 | 0.16 | 0.12 | 0.14 | 0.09 |
|  | (0.19–0.22) | (0.14–0.18) | (0.11–0.14) | (0.10–19) | (0.08–0.10) |
| Brain | 0.62 | 0.16 | 0.12 | 0.12 | 0.09 |
|  | (0.53–0.76) | (0.15–0.16) | (0.10–0.13) | (9.09–0.15) | (9–08–0.10) |
| S/Cereb | 1.98 | 3.5 | 3.0 | 1.25 | 1.8 |
| S/Cx | 1.27 | 1.93 | 1.57 | 0.94 | 1.29 |

To determine the in vivo specificity of FBNT analogs [$^{18}$F] 6a, 6d and 6e for rat brain DAT, a series of studies were performed in which unlabeled DAT specific ligand RTI-113 (5 mg of ligand per kg body weight of rat) was intravenously administered 15 minutes prior to the intravenous administration of [$^{18}$F] 6a, 6d and 6e. The rats were sacrificed 60 minutes after injection of [$^{18}$F] 6a, 6d and 6e and the striatum, prefrontal cortex, and cerebellum were dissected and the uptake of radioactivity determined. The results of this study, shown in Tables 2, 3 and 5, clearly demonstrate that RTI-113, the DAT ligand, significantly blocked the uptake of [$^{18}$F] 6a, 6d and 6e, in the DAT transporter rich striatum.

To determine the in vivo selectivity of FBCINT (6d) for rat brain DAT, a series of studies were performed in which unlabeled monoamine transporter specific ligands (5 mg of ligand per kg body weight of rat) were intravenously administered 15 minutes prior to the intravenous administration of [$^{18}$F] FBCINT. The rats were sacrificed 60 minutes after injection of [$^{18}$F] FBCINT and the striatum, cortex, prefrontal cortex, olfactory tubercles and cerebellum were dissected and the uptake of radioactivity determined. The monoamine transporter ligands administered were RTI-113 (DAT), paroxetine (SERT) and reboxetine (NET). The results of this study, shown in Table 4, clearly demonstrate that only GBR 12909, the DAT ligand, significantly blocked the uptake of [$^{18}$F] FBCINT in the DAT transporter rich striatum and olfactory tubercles. The SERT and NET blocking agents showed no effect on the regional brain uptake of [$^{18}$F] FBCINT. These preliminary data strongly suggested that E-[$^{18}$F] FBCINT (6d) was the best of the candidate (N-((E) 4-fluorobut-2-en-1-yl)-2β-carbomethoxy-3β-(4-substituted-phenyl)nortropanes for PET. The data in Tables 2, 3, 4 and 5 can be used in art-known computer programs to calculate estimates for human dosages.

Figure 1:
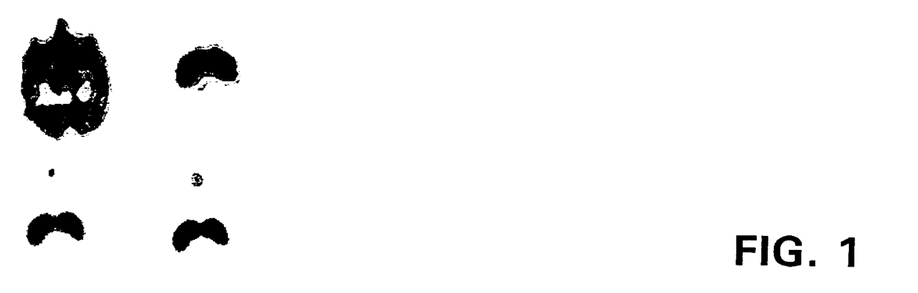
FIG. 1 is an in vivo imaging study with E-[$^{18}$F]FBCINT (6d) in a Rhesus monkey demonstrating high striatum uptake. The image times were: top left—12–15 min.; top right—30–60 min.; bottom left—2–2.5 h; bottom right—3–3.5 h.

The regional distribution of E-[$^{18}$F] FBCINT (6d) was studied in the brain of a rhesus monkey. Quantitative brain images were collected using a Siemens 951 31 slice PET imaging system. Dynamic emission data were acquired using a 35 frame acquisition protocol which included twelve 30 second scans, six one minute scans, six 3 minute scans, five 10 minute scans and six 20 minute scans. The regional distribution of radioactivity is (no partial volume correction was applied) expressed as nCi/mL after i.v. administration of E-[$^{18}$F] FBCINT (5.34 mCi). The striatum was the region of highest uptake in the brain and showed clear visualization at 30 minutes after injection (FIG. 1). Region of interest measurements determined striatum to cerebellum ratios to be 2.9, 11.7 and 14.2 at 0.5 hours, 2.25 hours and at 3.25 hours p.i. respectively (FIG. 1). These in vivo ratios were greater than [$^{18}$F] FECNT.

Figure 2:
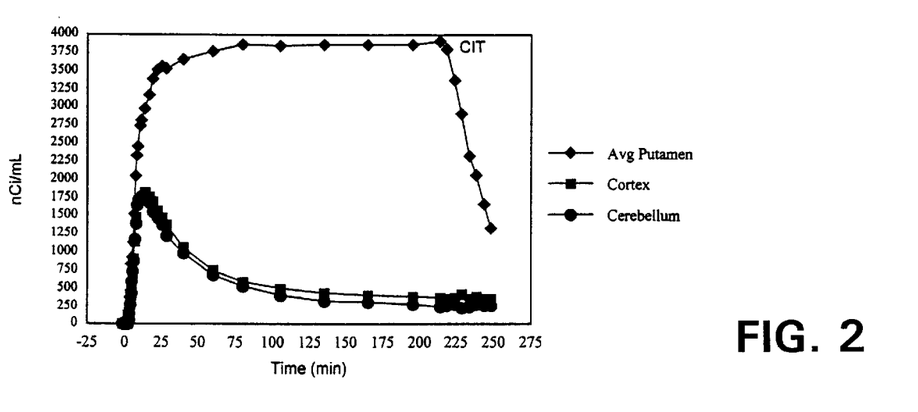
FIG. 2 is an in vivo imaging study with E-[$^{18}$F]FBCINT (6d) in a Rhesus monkey demonstrating 14:1 striatum to cerebellum ratios.
Figure 3:
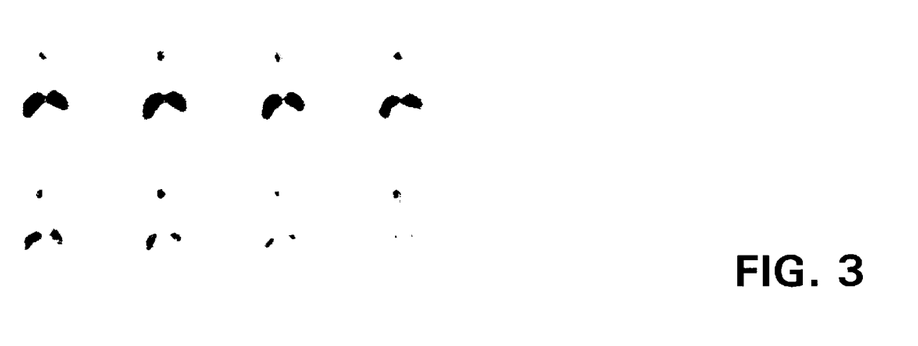
FIG. 3 shows the displacement E-[$^{18}$F]FBCINT (6d) by β-CIT resulting in striatal washout and demonstrating that 6d binds to striatal DAT.

A chase study with E-[$^{18}$F] FBCINT and β-CIT, a DAT ligand, was also performed in the same rhesus monkey. At 195 minutes p.i. 3.0 mg (0.9 μmol/kg) of β-CIT, was administered intravenously and dynamic imaging was continued for an additional 40 minutes (eight 5 minute scans). After 40 minutes following administration of β-CIT the PET images clearly showed a significant reduction of activity in the striatum (FIGS. 2 and 3). The displacement of E-[$^{18}$F] FBCINT (6d) by β-CIT resulted in a washout half-time of 21 minutes. The regional distribution and kinetic behavior of E-[$^{18}$F] FBNT (6a), E-[$^{18}$F] FBCINT (6d), and E-[$^{18}$F] FBFNT (6e) were next compared in the brain of awake rhesus monkeys.

Figure 4:
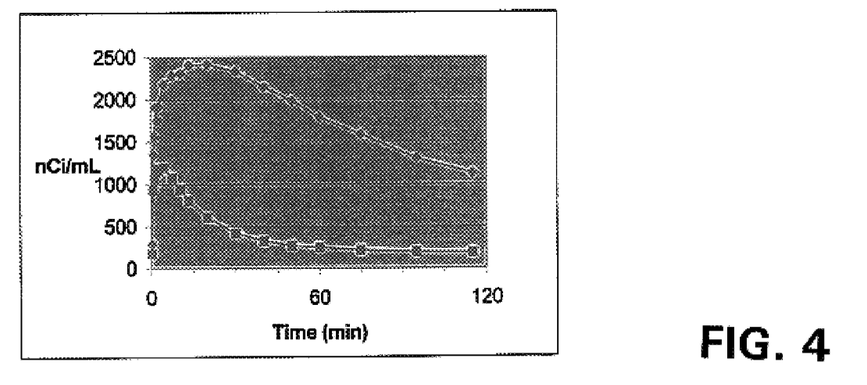
FIG. 4 is an in vivo imaging study with E-[$^{18}$F]FBFNT (6e) in an awake Rhesus monkey demonstrating transient equilibrium which was achieved at 30 min. post injection. The diamond symbol represents striatum and the square symbol cerebellum.
Figure 5:
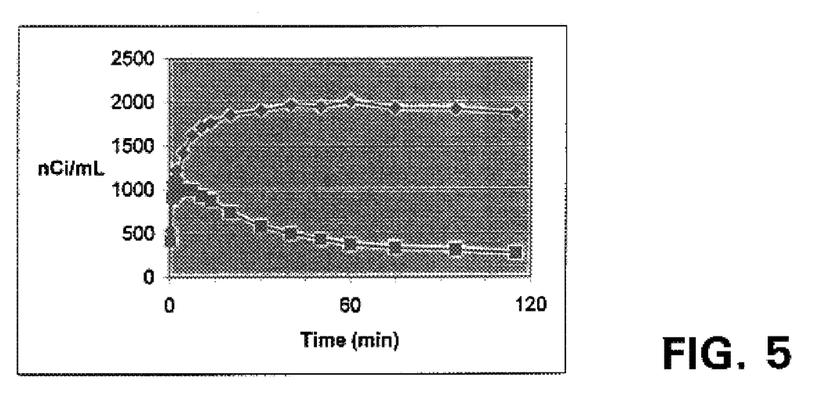
FIG. 5 is an in vivo imaging study with E-[$^{18}$F]FBCINT (6d) in an awake Rhesus monkey demonstrating very little if any washout. The diamond symbol represents striatum and the square symbol cerebellum.

The regional kinetics of [$^{18}$F] 6e and [$^{18}$F] 6d in the brain of awake rhesus monkeys are shown in FIGS. 5 and 4 respectively. Both [$^{18}$F] 6f and [$^{18}$F] 6d exhibited high initial uptake in the striatum and very little uptake in the cerebellum. [$^{18}$F] FBNT (6a) was evaluated in an awake rhesus monkey; however, the images showed no visible retention of radioactivity in the striatum. The peak uptake ratio of striatumwcerebellum was 4:1 at 20 minutes for [$^{18}$F] 6f and was 5:1 at 100 minutes for [$^{18}$F] 6d. The in vivo ratio of

[1¹⁸F] FBFNT (6e) was slightly than [¹⁸F] FECNT, 5:1. [¹⁸F] FBFNT (6e) reached a transient equilibrium in the striatum at 20 minutes post injection, whereas the decay corrected uptake of [¹⁸F] FBCINT (6d) appears constant at 115 minutes post injection.

In summary, a series of (N-((E)-4-fluorobut-2-en-1-yl)-2β-carbomethoxy-3β(4-substituted-phenyl)nortropanes (FBNT) were synthesized and evaluated for the monoamine transporter affinity using in vitro competitive binding as potential DAT PET imaging agents. These studies demonstrated that only analogues 6a (X=H), 6d (X=Cl) and 6e (X=F) exhibited very high selectivity for DAT. Analogues 6a, 6d and 6e also showed moderate to high Ki (nM) for DAT 7.52, 2.54 and 1.7 respectively and indicated potential for achieving an early transient equilibrium at the DAT which is most desirable for kinetic modeling. Fluorine-18 labeled 6a, 6d and 6e were prepared in a 2-step reaction sequence and in good 10% RCY. In PET imaging in awake rhesus monkeys, only fluorine-18 labeled FBFNT (6e), an altropane analog, achieved an early transient equilibrium at the striatal DAT. These studies show that fluorine-18 labeled FBFNT is an excellent candidate, possessing kinetic properties comparable to but no better than [¹⁸F] FECNT for in vivo quantitation of DAT by PET imaging.

It will be understood that compounds of the invention can be labeled with an isotope of any atom or combination of atoms in the structure. While ¹⁸F has been emphasized herein as being particularly useful for PET imaging, other uses are contemplated and will be apparent to those skilled in the art. For example, without limitation, compounds of the invention can be labeled with ¹⁴C to provide a tracer useful for biochemical studies of dopamine transporter. In addition, the binding studies reported herein demonstrate a pharmacological effect of compounds of the invention which can be utilized for physiological and behavioral studies and therapies, as will be apparent to those skilled in the art.

All references cited in this application are specifically incorporated in their entirety by reference herein.

The following examples illustrate the invention but are in no way intended to limit the scope of the invention.

EXAMPLES (E)-2-Buten-1,4-diol:

To a suspension of LiAlH$_4$ (3.8g, 99 mmol) in 100 mL of THF was added a solution of 2-butyne-1,4-diol (5.7 g, 66 mmol) under stirring. The resulting mixture was refluxed for 4 hours. After cooling to ambient temperature water was added dropwise carefully until no further reaction was observed (about 8 mL of water used). The slurry was filtered through celite and washed with diethyl ether for three times. Evaporation of the solvents and thorough drying in vacuo gave the product as a liquid (3.5 g, 60%) $^1$H NMR (300MHz, CDCl$_3$) δ 5.90–5.89 (m, 2H), 4.17 (d, J=2.1 Hz, 4H), 1.92 (broad, 2H).

(E)-1,4-Ditosyloxy-2-butene:

To a solution of (E)-2-buten-1,4-diol (326 mg, 3.7 mmol) and p-toluenesulfonyl chloride (1.76 g, 9.25 mmol) in 30 mL of THF was added portionwise sodium tert-butoxide (1.07 g, 11.1 mmol)) under stirring at 0° C. The mixture was then stirred overnight at rt. Water (100 mL) was added and the product was extracted with CH$_2$CL$_2$ (3×25 mL). The extract was dried with MgSO$_4$, filtered, and evaporated. Purification by flash column chromatography with hexane:ether:CH$_2$CH$_2$/3:1:1 gave the product as a crystal (1.21 g, 182%), m.p. 90–91° C. $^1$H NMR (300 MHz, CDCl$_3$) δ 7.77 (d, J=8.7 Hz, 4H), 7.35 (d, J–8.4 Hz, 4H), 5.75–5.73 (m, 2H), 4.49–4.47 (m, 4H), 2.46 (s, 6H; Anal. Calcd for C$_{18}$H$_{20}$O$_6$S$_2$: C, 54.53; H, 5,08,found C, 54.61; H, 5.07.

(E)-1-Fluoro-4-tosyloxy-2-butene:

To a solution of (E)-1,4-ditosyloxy-2-butene (256 mg, 0.64 mmol) in 10 mL of THF was added Bu$_4$NF (0.7 mL, 1M in THF, 0.7 mmol). The mixture was heated to reflux for 30 min. Evaporation and purification of the residue by flash column chromatography with hexane:ether/2:1 afforded the product as a colorless oil (60 mg, 38%). $^1$ H NMR (CDCl$_3$, 300 MHz) δ 7.80 (d, J=8.4 Hz, 2H), 7.36 (d, J=8.4 Hz, 2H), 5.99–5.75 (m, 2H, 4.84 (ddd, J$_{FCH}$=46.5 Hz, J=4.8, 1.2 Hz, 2H), 4.59–4.56 (m, 2H), 2.46 (s, 3H).

(Z)-1,4-Ditosyloxy-2-butene:

This compound was prepared using the same procedure as the trans compound was made (29%). $^1$H NMR (CDCl$_3$, 300 MHz) δ 7.76 (d, J–7.8 Hz, 4H), 7.35 (d,J=7.8 Hz, 4H), 5.69–5.66 (m, 2H), 4.54–4.52 (m, 4H), 2.45 (s, 6H; $^{13}$C NMR (75 Hz, CDCl$_3$δ 145.08, 132.66, 129.88, 127.75, 127.48, 64.76, 21.55.

(Z)-1-Fluoro-4-tosyloxy-2-butene:

This compound was prepared using the same procedure as the trans compound was made (29%). Colorless oil. $^1$H NMR (CDCl$_3$, 300 MHz) δ 7.79 (d, J=8.1 Hz, 2H), 7.36 (d, J=7.8 Hz, 2H), 5.89–5.65 (m, 2H), 4.92 (dd, J$_{FCH}$=46.5, J=5.4 Hz, 2H), 4.65 (d, J=5.1 Hz, 2H), 2.46 (s, 3H); $^{13}$C NMR (75 Hz, CDCl$_3$ $_δ$ 145.00, 132.86, 129.86, 129.63 (d, J$_{FCC}$=19.05 Hz), 125.85 (d, J$_{FCCC}$=9.3 Hz), 78.54 (d, J$_{FC}$=164.3 Hz), 65.43, 21.57.

2-Carbomethoxy-3-(4'-trimethylsilylphenyl)tropane (2):

To a Grignard solution of 4-methylsilylphenyl magnesium bromide prepared from 1.2 g of Mg (49 mmol) and 9 g of 4-bromotrimethylsilylbenzene (39 mmol) in 10 mL of ether was added (R)-(−)anhydroecognine methyl ester (2.285 g, 12.6 mmol) in 10 mL of ether at −60° C. under argon. After addition the reaction mixture was stirred at −40° C. for 2.5 hrs. The resulting mixture was cooled to −78° C. and treated dropwise with a solution of TFA (3.1 mL) in 10 mL of dry Et$_2$O while the temperature was maintained. The mixture was warmed to 0 C and 40 mL of H$_2$O was added. The aqueous phase was separated and the organic phase was extracted with 3N HCl (2×20 mL). The combined extract was basified with concentrated NH$_4$OH (pH=9), extracted with CH$_2$Cl$_2$, dried, and evaporated in vacua. Purification by chromatographic column with 10% MeOH in CH$_2$CL$_2$ afforded the product (oil, 3.1, 74%).

2β-Carbomethoxy-3β(4'-bromophenyl)tropane (3b):

A mixture of 2β-Carbomethoxy-3β-(4'-trimethylsilylphenyl)tropane (594 mg, 1.79 mmol) and KBr (320 mg, 2.68 mmol) in 15 mL of acetic acid and 2 mL of MeOH was stirred at 60° C. for 20 min. 285 mg of NCS (2.15 mmol) was added at one time and the resulting mixture was stirred at the same temperature for 4 hrs. After cooling to rt 100 mL of H$_2$O and 50 mL of Et$_2$O were added. The aqueous phase was separated and the organic phase was extracted with 3N HCl (20 mL). The combined aqueous phase was washed with 20 mL of Et$_2$O, basified with concentrated NH$_4$OH and extracted with CH$_2$Cl$_2$ (2×50 mL). The solution was then dried and the removal of the solvent in vacuo gave the pure product as a white solid (607 mg, 100%). m.p. 114–116° C. $^1$H NMR (CDCl$_3$, 400 MHz) δ 7.38 (d, J=8.4 Hz, 2H), 7.13 (d, J=8.4 Hz, 1H), 3.58–3.55 (m, 1H), 3.51 (s, 3H), 3.38–3.36 (m, 1H), 2.98–2.86 (m, 2H), 2.56 (dt, J–12.8, 2.8 Hz, 1H), 2.23 (s, 3H), 2.26.2.05 (m, 2H), 1.75–1.58 (m, 3H).

N-(2,2,2trichloroethylcarbamoyl)-2β-carbomethoxy-3β-(4-bromophenyl)nortropane (4b):

Treatment of 2β-carbomethoxy-3β-(4 '-bromophenyl)tropane with TrocCl at 150° C. for 3.5 hrs afforded the product as a Colorless oil (82%) after chromatographic purification (hexane:ether/3:1), ¹H NMR (CDCl₃, 300 MHz) δ 7.42–7.39 (m, 2H), 7.13–7.09 (m, 2H), 4.96–4.40 (m, 4H), 3.45 and 3.43 (s, 3H), 3.27–3.21 (m, 1H), 2.92–2.75 (m, 2H), 2.27–1.68 (m, 5H).

2β-carbomethoxy-3β-(4'-bromophenyl)nortropane (5b):

Treatment of N-(2,2,2-trichloroethylcarbamoyl)-2β-carbomethoxy-3β-(4'-bromophenyl)nortropane with Zn/CH₃COOH for 20 hrs afforded the product as a white solid (90%). m.p. 122–124° C. ¹H NMR (CDCl₃, 300 MHz) δ 7.40 (d, J=8.4 Hz, 2H), 7.05 (d, J=8.4 Hz, 2H), 4.65 (br, 1H), 3.88 (br, 2H), 3.40 (s, 3H), 3.26–3.18 (m, 1H), 2.79(br, 1 H), 2.49–1.72 (m, 6H).

2-Carbomethoxy-3-(4'-iodophenyl)tropane (3c):

This compound was synthesized by the reaction of 2-Carbomethoxy-3-(4'-trimethylsilylphenyl)tropane with I₂ in the presence of AgBF₄ in MeOH as a solvent at 0 C. -rt (74%).

2β-Carbomethoxy-3β-(4'-iodophenyl)tropane (3c):

White solid. ¹H NMR (CDCl₃, 3200 MHz) δ 7.59 (d, J–8.1 Hz, 2H), 6.92 (d, J–8.1 Hz, 2H), 3.87 (br. 3H), 3.39 (s, 3H), 3.21–3.15 (m, 1H), 2.76 (br, 1H), 2.46–1.68 (m, 6H).

2-Carbomethoxy-3β(4'-iodophenyl)nortropane (5c):

White solid. ¹H NMR (CDCl₃, 300 MHz) δ 7.59 (d, J=8.1 Hz, 2H), 6.92 (d, J=8.1 Hz, 2H), 3.87 (br. 3H), 3.39 (s, 3H), 3.21–3.15 (m, 1H), 2.76 (br, 1H), 2.46–1.68 (m, 6H).

2β-Carbomethoxy-3β-phenyltropane (3a):

This compound was synthesized using a similar reaction as 2β-Carbomethoxy-3β-(4'-trimethylsilylphenyl)tropane starting with anhydroecognine methyl ester and phenylmagnesium bromide.

2β-Carbomethoxy-3β-phenylnortropane (5a) (63%):

¹H NMR (CDCl₃, 300 MHz) δ 7.33–7.16 (m, 5H), 5.39–5.27 (br, 1H), 3.95–3.88 (m, 2H), 3.37 (s, 3H), 3.32–3.28 (m, 1H), 2.81–2.80 (m, 1H), 2.57–2.47 (m, 1H), 2.37–1.71 (m, 5H).

2β-Carbomethoxy-3β(4'-fluorophenyl)tropane (5e):

This compound was synthesized using a similar reaction as 2β-Carbomethoxy-3β-(4'-trimethylsilylphenyl)tropane starting with anhydroecognine methyl ester and 4-fluorophenylmagnesium bromide.

N-(2,2,2-trichloroethylcarbamoyl)-2β-Carbomethoxy-3β-(4'-fluorophenyl)nortropane (4e) (86%):

Colorless oil. ¹H NMR (300 MHz, CDCl₃) δ 7.22–7.17 (m, 2H), 6.96 (t, J=8.7 Hz, 2H), 4.96–4.40 (m, 2H), 3.44 and 3.41 (s, 3H), 3.30–3.25 (m, 1H), 2.92–2.76 (m, 2H), 2.25–1.69 (m, 5H).

2β-Carbomethoxy-3β-(4'-fluorophenyl)nortropane (45e) (77%):

White solid, mp 107–110° C. ¹H NMR (300 MHz, CDCl₃ δ 7.15(dd, J=8.4, 5.4 Hz, 2H), 6.97 (t, J=8.7 Hz, 2H), 4.34 (broad, 1H), 3.80–3.73 (m, 2H), 3.38 (s, 3H), 3.28–3.20 (m, 1H), 2.74–2.72 (m, 1H), 2.45–2.36 (m, 1H), 2.20–2.00 (m, 2H), 1.82–1.62 (m, 3H).

N-((E)-4-fluorobut-2-en-1-yl)-2β-carbomethoxy-3β-(4-iodophenyl)nortropane (6c):

A mixture of 2β-carbomethoxy-3β-(4-iodophenyl) nortropane (15 mg, 0.054 mmol) and (E)-1-fluoro-4-tosyloxy-2-butene in 2 mL of acetonitrile containing NaHCO₃ (5 mg, 0.059 mmol) and a catalytic amount of KI was heated to 70° C. for 1.5 hour. The mixture was poured into 15 ml of H₂O containing 3 mL of 5% NaHCO₃ and extracted with CH₂CL₂ (3×5 mL). After drying and evaporation of the solvent, purification of the residue by TLC plates with 5% MeOH in CH₂Cl₂ (3×5 mL). After drying and evaporation of the solvent, purification of the residue by TLC plates with 5% MeOH in CH₂Cl₂ gave the product as a white solid (15 mg, 84%). ¹H NMR (CDCl₃, 300 MHz) δ 7.59 (d, J=8.1 Hz, 2H), 7.58 (d, J=8.1 Hz, 2H), 7.01 (d, J=8.1 Hz, 2H), 5.88–5.79 (m, 2H), 4.92–4.76 (m, 2H), 3.70–3.48 (m, 2H), 3.50 (s, 3H), 3.03–2.88 (m, 4H), 2.63–2.54 (m, 1H), 2.19–1.60 (m, 5H).

The following four compounds were synthesized by following the same procedures as above.

N-((E)-4-=fluorobut-2-en-1-yl)-2β-carbomethoxy-3β-4-(4-bromophenyl)nortropane (6b):

Colorless oil. ¹H NMR (CDCl₃, 300 MHz) δ 7.38 (d, J=8.4 Hz, 2H), 7.13 (d, J=8.4 Hz, 2H), 5.82–5.78 (m, 2H), 4.92–4.75 (m, 2H), 3.68–3.40 (m, 2H), 3.50 (s, 3H), 3.00–2.86 (m, 4H), 2.63–2.54 (m, 1H), 2.14–1.65 (m, 5H).

N-((E)-4-fluorobut-2-en-1-yl)-2β-carbomethoxy-3β-phenylnortropane (6a):

Colorless oil. ¹H NMR (CDCl₃, 300 MHz) δ 7.29–7.13 (m, 5H), 5.82–5.77 (m, 2H), 4.92–4.75 (m, 2H), 3.69–3.42 (m, 2H), 3.48 (s, 3H), 3.08–2.59 (m, 5H), 2.14–1.60 (m, 5H).

N-((E)-4-fluorobut-2-en-1-yl)-2β-carbomethoxy-3β-(4-fluorophenyl)nortropane (6e):

Colorless oil. ¹H NMR (300 MHz, CDCl₃ δ 7.22 (dd, J=8.4, 5.4 Hz, 2H), 6.98–6.93 (m, 2H), 5.80–5.76 (m, 2H), 4.91 (d, J=4.8 Hz, 1H), 4.76–4.75 (m, 1H), 3.68 (m, 1H), 3.50 (s, 3H), 3.43–3.42 (m, 1H), 3.07–2.84 (m, 4H), 2.60 (td, J=12.6, 3 Hz, 1H), 2.16–1.96 (m, 2H), 1.79–1.59 (m, 3H); HRMS Calcd for C₁₉H₂₃F₂NO₂ 335.1697, found 335.1681.

N-((E)-4-fluorobut-2-en-1-yl)-2β-carbomethoxy-3β-(4-chlorophenyl)nortropane (6c):

We claim:

1. A compound of the following formula:

ᵃF(CH₂)R(CH₂)—N—CO₂CH₃, X

Where R is C₂–C₆ mono- or multi-unsaturated hydrocarbon having one or more ethylene, acetylene or allene groups, a is 18 or 19, and X is H or halogen.

2. The compound of claim 1 wherein X is in the 4' position.

3. The compound of claim 1 wherein a is 18.

4. The compound of claim 1 wherein R is C₂–C₆ mono- or multi-unsaturated hydrocarbon having one or more ethylene.

5. The compound of claim 4 wherein a is 18.

6. The compound of claim 4 wherein R is selected from the group consisting of —CH =CH—, —CH =CH—CH₂—, —CH₂—CH =CH—, —CH =CH—CH₂—CH₂—, —CH₂—CH =CH—CH₂—, —CH₂—CH₂—CH =CH—, —CH =CH—(CH₂)₃ ₒᵣ ₄—, —CH₂—CH =CH—(CH₂)₂ ₒᵣ ₃—, —(CH₂)₂—CH =CH—CH₂—, —(CH₂)₃—CH =CH—, —CH =CH—CH =CH—, —CH =CH—CH =CH—CH₂—, —CH =CH—CH₂—CH =CH—, and —CH =CH—CH =CH—CH =CH—.

7. The compound of claim 6 wherein a is 18.

8. The compound of claim 1 wherein R is Chd 2–C₆ mono- or multi-unsaturated hydrocarbon having one or more acetylene.

9. The compound of claim 8 wherein a is 18.

10. The compound of claim 8 wherein R is selected from the group consisting of —C ≡C—, —C ≡C—CH₂—, —CH₂—C≡C—, —C≡C—CH₂—CH₂—, —CH₂—C≡C—CH₂—, —CH₂—CH₂—C≡C—, —C≡C—(CH₂)₃ ₒᵣ ₄-, —CH₂—C≡C—(CH₂)₂ ₒᵣ ₃-, —CH₂—C≡C—(CH₂)₁ ₒᵣ ₂-, —(CH₂)₃—C≡C—, —CH=CH—C≡C—, —C≡C—CH=CH-₂—, —C≡C—CH₂—CH=CH—, and —C≡C—CH₂—C≡C—CH₂—.

11. The compound of claim 10 wherein a is 18.

12. The compound of claim 1 wherein R is C₂–C₆ mono- or multi-unsaturated hydrocarbon having one or more allene.

13. The compound of claim 12 wherein a is 18.

14. The compound of claim 12 wherein R is selected from the group consisting of —CH=C=CH—CH₂—, —CH₂—CH=C=CH—, —CH=C=CH—(CH₂)₂ ₒᵣ ₃-, —CH₂—CH=C=CH—, (CH₂)₁ ₒᵣ ₂-, —(CH₂)₂—CH=C=CH—, —(CH₂)₂—CH=C=CH—CH₂—, —(CH₂)₃—CH=C=CH—, —CH=CH—CH₂—CH=C=CH—, —CH=C=CH—CH₂—C≡C—, and —C≡C—CH=C=CH—CH₂—.

15. The compound of claim 14 wherein a is 18.

16. The compound of claim 2 wherein X is H.

17. The compound of claim 2 wherein X is Cl.

18. The compound of claim 1 wherein R is CH=CH and a is 18.

19. The compound of claim 18 wherein X is H.

20. The compound of claim 18 wherein X is Br.

21. The compound of claim 18 wherein X is F.

22. The compound of claim 18 wherein X is Cl.

23. The compound of claim 22 wherein the compound is an E isomer.

24. A kit for rapid synthesis of a radioactively labeled compound, comprising (a) a compound having the structure:

wherein L is a leaving group which is displaced by a substituent containing a radiotracer atom, wherein said substituent is ¹⁸F(CH₂)R(CH₂), where R is C₂–C₆ mono- or multi-unsaturated hydrocarbon having one or more ethylene, acetylene or allene groups, (b) a reagent capable of displacing said L with said substituent.

25. A method of conducting positron emission tomography imaging of a subject comprising administering to said subject an image-generating amount of a compound according to claim 1 which contains at least one radioactive halogen, and measuring the distribution within the subject of said compound by positron emission tomography.

26. The method of claim 25 wherein the halogen is ¹⁸F and the distribution of the compound is measured by position emission tomography.

* * * * *

UNITED STATES PATENT AND TRADEMARK OFFICE
CERTIFICATE OF CORRECTION

PATENT NO.   : 6,344,179 B1
DATED        : February 5, 2002
INVENTOR(S)  : Goodman et al.

It is certified that error appears in the above-identified patent and that said Letters Patent is hereby corrected as shown below:

Title page,
Item [56], References Cited, OTHER PUBLICATIONS, please replace
"*Nature* 38:144-150" with -- *Nature* 379:606-612 --.

Column 2,
Line 38, please replace "more Gleffective therapeutic" with -- more effective therapeutic --.
Line 52, please replace "volunteersand" with -- volunteers and --.

Columns 7 and 8,
Scheme 1, the starting compound labeled 1, please delete the compound as shown and insert the following structure therefor:
--

--

Column 8,
Lines 7-9, please replace "(N-((E)-4-fluorobut-2-en-1-yl)-20βcarbomethoxy-3β-(4-substituted-phenyl) nortropanes (FBNT)" with -- (N-((E)-4-fluorobut-2-en-1-yl)-2βcarbomethoxy-3β-(4-substituted-phenyl) nortropanes (FBNT) --.

Column 14,
Line 66, please replace "striatumwcerebellum" with -- striatum/cerebellum --.

Column 15,
Line 1, please replace "[1$^{18}$F]FBFNT (6e) was slightly than" with -- [1$^{18}$F] FBFNT (6e) was slightly less than --.

UNITED STATES PATENT AND TRADEMARK OFFICE
CERTIFICATE OF CORRECTION

PATENT NO. : 6,344,179 B1
DATED : February 5, 2002
INVENTOR(S) : Goodman et al.

It is certified that error appears in the above-identified patent and that said Letters Patent is hereby corrected as shown below:

Column 18,
Line 62, please delete "wherein R is Chd 2-$C_6$" and insert -- wherein R is $C_2$-$C_6$ --.

Column 19,
Lines 14 and 15, please delete "-$CH_2$-CH=C=CH-,(CH2)1or2-," and insert
-- -$CH_2$-CH=C=CH-$(CH_2)_{1\ OR\ 2}$-, --.

Signed and Sealed this

Eighth Day of October, 2002

Attest:

Attesting Officer

JAMES E. ROGAN
Director of the United States Patent and Trademark Office